(12) United States Patent
Arras et al.

(10) Patent No.: US 8,906,321 B2
(45) Date of Patent: Dec. 9, 2014

(54) REAGENT KIT WITH IN-TRANSIT SECURING MEANS

(71) Applicant: Roche Diagnostics Operations, Inc., Indianapolis, IN (US)

(72) Inventors: Georg Werner Arras, Reichelsheim (DE); Bernd Drescher, Oberhausen (DE); Frank-Rainer Jaehde, Mannheim (DE); Hans-Juergen Mueller, Bernried (DE); Klaus Oswald, Riedstadt (DE); Gottfried Senftner, Lampertheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/629,852

(22) Filed: Sep. 28, 2012

(65) Prior Publication Data

US 2013/0064735 A1 Mar. 14, 2013

Related U.S. Application Data

(63) Continuation of application No. PCT/EP2011/054919, filed on Mar. 30, 2011.

(30) Foreign Application Priority Data

Mar. 31, 2010 (EP) .................................. 10158662

(51) Int. Cl.
*B65D 43/08* (2006.01)
*G01N 35/10* (2006.01)
*B65D 47/08* (2006.01)
*B01L 3/00* (2006.01)
*G01N 35/04* (2006.01)

(52) U.S. Cl.
CPC ........ *B65D 47/0866* (2013.01); *G01N 35/1002* (2013.01); *B01L 2200/025* (2013.01); *B01L 2200/18* (2013.01); *G01N 2035/0405* (2013.01); *B01L 3/523* (2013.01); *B01L 2300/043* (2013.01); *B01L 3/527* (2013.01); *B01L 2200/142* (2013.01)
USPC .......... 422/430; 422/501; 215/237; 220/23.4; 220/502; 435/304.1; 435/305.3

(58) Field of Classification Search
USPC ........... 422/64, 562, 509, 400, 102, 401, 550, 422/430; 220/23.4, 253, 23.89
See application file for complete search history.

(56) References Cited

U.S. PATENT DOCUMENTS 3,981,419 A 9/1976 Nilson
5,540,890 A 7/1996 Clark et al.
(Continued)

FOREIGN PATENT DOCUMENTS

CN 2249214 Y 3/1997
CN 1624485 A 6/2005
(Continued)

*Primary Examiner* — Sally Merkling
(74) *Attorney, Agent, or Firm* — Roche Diagnostics Operations, Inc.

(57) ABSTRACT

A reagent kit comprising: a reagent container assembly with at least one reagent container, wherein the reagent container has at least one container body and at least one closure which can be mounted or provided on the container body. The closure comprises a closure base member and a lid which is mounted movably on the base member for movement at least between a closed lid position and another lid position, and an in-transit securing means mountable in a locking position on the reagent container and which is movable relative to the reagent container from the locking position into a release position. The in-transit securing means, when in the locking position, secures the lid in the closed lid position. By moving the in-transit securing means from the locking position into the release position, the lid is moved from the closed lid position into the other lid position.

14 Claims, 14 Drawing Sheets

(56) References Cited

U.S. PATENT DOCUMENTS

| | | |
|---|---|---|
| 5,628,962 A | 5/1997 | Kanbara et al. |
| 5,632,399 A | 5/1997 | Palmieri et al. |
| 5,862,934 A * | 1/1999 | Sattler et al. ............. 220/23.4 |
| 5,901,885 A | 5/1999 | Iida |
| 6,149,866 A | 11/2000 | Luotola et al. |
| 6,265,225 B1 | 7/2001 | Otto et al. |
| 6,864,100 B1 | 3/2005 | Ribbe et al. |
| 7,371,355 B2 | 5/2008 | Takahashi et al. |
| 7,488,453 B2 | 2/2009 | Takahashi et al. |
| 7,785,537 B2 | 8/2010 | Ohashi |
| 7,799,284 B2 | 9/2010 | Ohashi et al. |
| 7,931,879 B2 * | 4/2011 | D'Amore et al. ............. 422/550 |
| 2005/0142040 A1 | 6/2005 | Hanawa et al. |
| 2005/0170356 A1 | 8/2005 | Kureshy et al. |
| 2010/0034700 A1 | 2/2010 | Rousseau et al. |

FOREIGN PATENT DOCUMENTS

| | | |
|---|---|---|
| EP | 0521299 A2 | 1/1993 |
| EP | 0543638 A1 | 5/1993 |
| EP | 0703457 A2 | 3/1996 |
| EP | 0714834 A1 | 6/1996 |
| EP | 1424291 A1 | 6/2004 |
| EP | 1916200 A1 | 4/2008 |
| GB | 1522128 A | 8/1978 |
| WO | 92/20449 A1 | 11/1992 |
| WO | 95/01919 A1 | 1/1995 |
| WO | 2008/009821 A1 | 1/2008 |

\* cited by examiner

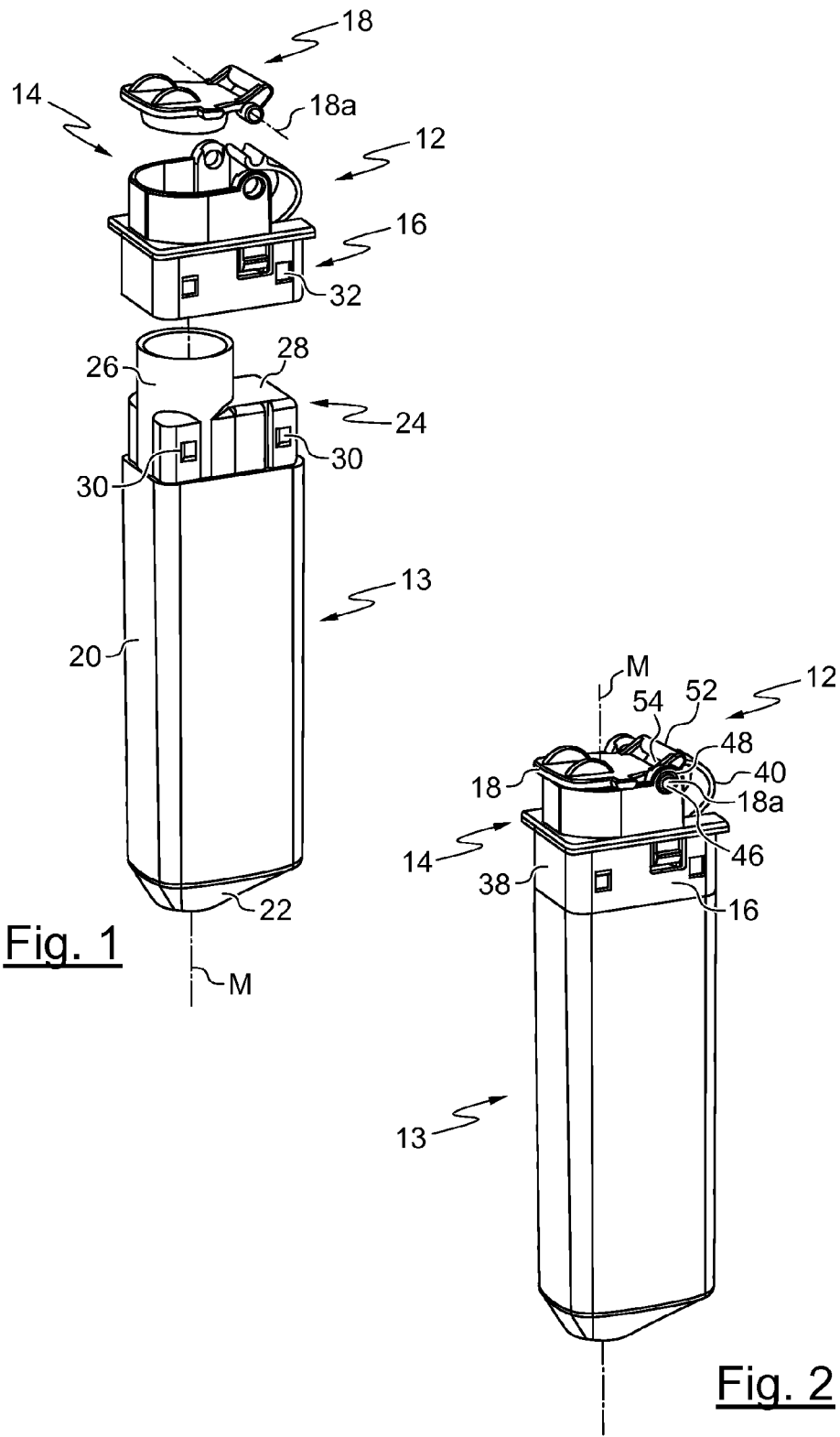

REAGENT KIT WITH IN-TRANSIT SECURING MEANS

CROSS-REFERENCE TO RELATED APPLICATIONS

This application is a continuation of International Application No. PCT/EP2011/054919, filed 30 Mar. 2011, which claims the benefit of European Patent Application No. 10158662.6, filed 31 Mar. 2010, the disclosures of which are hereby incorporated by reference in their entirety.

BACKGROUND

The present disclosure relates to reagent kits and, in particular, to reagent kits with in-transit securing means.

Reagent containers can be used in particular in the field of automatic analysis. Automatic analysis systems, for example diagnostic assay systems, require a plurality of different reagents (substances) for carrying out tests. These reagents are usually filled in individual containers, identified and, optionally, a plurality of individual containers with different reagents, which are calibrated to one another, are arranged to form a reagent container assembly for a specific test.

In order to ensure that, even when in transit to the user, the substances do not escape from the reagent containers, the reagent container assemblies are usually provided with in-transit securing means.

Reagent kits have been disclosed which in each case comprise a separate screw cap that can be screwed onto the respective container body in place of the closure provided for the analysis operation, and in its locking position, i.e., in the screwed-on position, the screw cap prevents the substance from escaping from the container body, even whilst in transit from the producer to the user.

Only when these reagent kits have reached the user, the in-transit securing screw caps are replaced by the closures which remain on the container bodies during the automatic analysis and can be opened and, optionally also closed again, by the automatic analysis system.

Other generic reagent kits have been disclosed in which the closure is already situated on the container body whilst in transit and the reagent container is additionally secured by the in-transit securing means which, in the locking position, secures the lid of the closure in the closed lid position. One such reagent container assembly comprises a plurality of reagent containers which can be opened and closed by a common sliding lid, wherein the reagent container assembly is secured whilst in transit by a detachable foil as in-transit securing means. The other disclosed reagent container is provided with a closure, into which an additional closure plate can be inserted for transportation.

Before using the above-described reagent container assemblies in an automatic analysis system, it is advantageous to move the lid of the closure at least once out of the closed lid position, i.e., to carry out an initial opening so as to equalize, for example, different pressure conditions inside and outside the container, and thereby enable the reagent container to be easily opened in the automatic analysis operation. This initial opening can in principle be affected by the analysis system or by the user.

The drawback of an initial opening by the analysis system is the relatively high force to be applied, which requires a correspondingly complicated and expensive opening mechanism of the analysis system and restricts the configuration of the analysis system in respect of the size and positioning of the individual elements. Furthermore, any fault or breakdown in the mechanism for the initial opening would mean a fault or breakdown in the entire analysis system.

The initial opening of the individual containers by the user, e.g., immediately before the insertion of the reagent container assembly into the analysis system, is also time-consuming and additionally susceptible to faults. For example, if the user does not remove or does not completely remove the in-transit securing means, the analysis system can even be damaged.

SUMMARY

It is against the above background that the embodiments of the present disclosure provide certain unobvious advantages and advancements over the prior art. In particular, the applicant has recognized a need for improvements in reagent kits with in-transit securing means.

Although the embodiments of the present disclosure are not limited to specific advantages or functionality, it is noted that the present disclosure facilitates the above-described initial opening.

In accordance with one embodiment of the present disclosure, a reagent kit is provided which comprises a reagent container assembly with at least one reagent container for accommodating a substance, the reagent container including at least one container body and at least one closure which is associated with the container body and which is mountable or provided thereon, wherein the closure comprises a closure base member and a lid supported movably on the closure base member for movement at least between a closed lid position and another lid position. The reagent kit also comprises an in-transit securing means which is mountable or mounted on the reagent container assembly in a locking position and which, when mounted on the reagent container assembly, is movable from the locking position into a release position relative to the reagent container assembly, wherein, in the locking position, the in-transit securing means secures the lid in the closed lid position.

The reagent container is designed to accommodate a typically fluid substance. However, the disclosure relates to reagent kits irrespective of whether the reagent container is filled with a substance or not.

The closure may be formed in one piece with the container body. However, in order to simplify the production of the reagent containers, in particular the production by injection-molding, the closure may be formed separately from the container body and may be mountable thereon, for example by being screwed or clipped thereon. Likewise, the closure base member and the lid can be formed in one piece or separately.

In a generic reagent kit, by moving the in-transit securing means relative to the reagent container assembly from the locking position into the release position, the lid is moved from the closed lid position into the other lid position.

In this way, the unlocking of the in-transit securing means, which is in any case necessary, and optionally its removal is combined with the initial opening so that the user, before inserting the reagent kit according to the disclosure into the analysis system, merely has to unlock and optionally remove the in-transit securing means.

In principle, provision can be made for the in-transit securing means to remain in the release position on the reagent container assembly, so that the reagent container assembly and the in-transit securing means can be handled as a unit even in the analysis operation.

However, since in automated analysis systems always as many reagent kits as possible are to be used so as to enable a large number of different tests to be performed, and since the in-transit securing means increases the total volume of the reagent kit, for space-saving reasons it may be advantageous to enable the in-transit securing means to be removed from the reagent container assembly out of the release position, so that the reagent container assembly can be inserted into the analysis system without the in-transit securing means.

In another embodiment, the in-transit securing means can be designed so that, when the in-transit securing means is situated in the locking position, the reagent kit meets certain demands concerning the fluid tightness of the container, e.g., so as to meet air-freight requirements, for example a 660 mbar pressure difference over 10 minutes.

With simpler reagent container assemblies, the lid can be displaceable between the closed lid position and an open position. In this case, the other lid position can be an opened position of the lid.

These and other features and advantages of the embodiments of the present disclosure will be more fully understood from the following detailed description taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which:

FIG. 1 shows the individual parts of a reagent container of a first embodiment of the present disclosure, in a view in perspective;

FIG. 2 shows the subject of FIG. 1 in the assembled condition;

Figure 3:
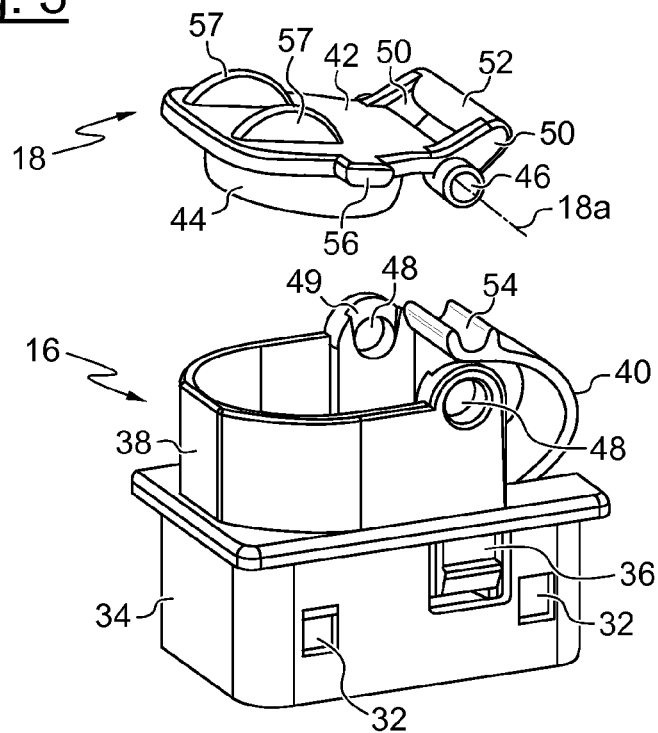
FIG. 3 shows an enlarged illustration of the individual parts of the closure from FIG. 1.

For reasons of clarity, not all the components are provided with reference numerals in each drawing, but only those components which are addressed in the description of the respective figure. In particular, in case there are several components of the same kind in one figure, not every component is denoted by a reference numeral.

Skilled artisans appreciate that elements in the figures are illustrated for simplicity and clarity and have not been drawn to scale. For example, the dimensions of some of the elements in the figures may be exaggerated relative to other elements to help improve understanding of the embodiment(s) of the present disclosure.

DETAILED DESCRIPTION

Reagent container assemblies usually remain for several weeks on an apparatus for automatic analysis. During this period it must be ensured that not too much of the filling substance escapes as a result of evaporation. For certain types of reagent, the gas transfer ($CO_2$ charge) from the ambient air is to be limited to a minimum.

To ensure adequate evaporation protection, reagent containers are known, for instance from DE 4439755 A1 or U.S. Pat. No. 5,540,890 B, in which, besides the closed lid position and an opened lid position, also an evaporation-protection position of the lid is provided, in which the lid rests only lightly on the closure base member or a neck of the container body.

For containers of this type, it is possible to provide for the other lid position to be an evaporation protection position and for the closed lid position to be an in-transit securing position, wherein the lid is movably mounted on the base member for movement between the in-transit securing position, the evaporation protection position and the opened lid position.

Upon removal of the in-transit securing means by the user, the lid is simultaneously moved out of the in-transit securing position and into the evaporation protection position, from which the automatic analysis system can displace the lid with low force input into the opened position.

It may be provided that in the in-transit securing position the lid is supported so securely on the closure base member or a neck of the container body, or is engaged therewith, that even if the reagent container topples over, no substance can escape. If a reagent container is not required for a relatively long time, it can be closed again at any time simply by displacing the lid into the in-transit securing position.

In order to reduce evaporation during the operation of the analysis system, without any once opened reagent containers having to be closed by the analysis system itself, the reagent kit can further comprise preloading means which preload the lid from the opened lid position into the evaporation protection position or, in the case of only two distinct lid positions, from the opened lid position into the closed lid position. Thereby, a mechanically self-closing lid is obtained.

With a view to an advantageous reduction in the number of components required, these preloading means can be formed in one piece with the closure base member. In this way a closure can be obtained which is assembled from only two parts. However, it is also possible for the preloading means to be separately formed and provided on the reagent kit. Alternatively, these preloading means can also be integrated into the analysis system, for example in the receptacle for a reagent container assembly.

A simple opening mechanism can be brought about in that the lid is pivotally mounted on the base member for pivotal movement about a lid axis.

In the case of pivotally mounted lids, the in-transit securing means can be realized in a structurally simple manner in that the in-transit securing means are movable by sliding displacement relative to the reagent container assembly in an unlocking direction from the locking position into the release position, wherein the in-transit securing means comprises at least one ramp-shaped engagement element for each lid, and the lid comprises at least one mating element cooperating with the engagement element in such a way that, upon sliding displacement of the in-transit securing means mounted on the reagent container assembly from the locking position in the unlocking direction, the engagement element and the mating element are in mutual sliding abutment engagement or come into mutual sliding abutment engagement so that, by sliding displacement of the in-transit securing means in the unlocking direction into the release position, the lid can be moved from the closed lid position into the other lid position.

While the in-transit securing means is being displaced from the locking position into the release position, the ramp-shaped engagement element can raise the mating element and thus the lid in a simple manner and can pivot the lid into the other lid position, for example the opened lid position or the evaporation protection position.

Another advantage of this design lies in that it can be easily operated by the user, who merely has to displace the in-transit securing means on the reagent container assembly so that, with a single movement, the in-transit securing means can be unlocked, optionally removed and the initial opening can be undertaken.

It is also possible that a plurality of engagement elements are provided on the in-transit securing means for one lid and associated mating elements are provided on the respective lid so as to prevent any tilting during the initial opening. For example, it is possible to provide on the lid two engagement tabs as engagement elements projecting from the lid on opposite sides parallel to the lid axis.

Usually, a plurality of different reagents are required for a given test and are assembled to form a test kit before delivery to the customer. Therefore, according to a typical embodiment of the present disclosure, the reagent container assembly comprises a plurality of reagent containers, typically 3 to 5 reagent containers, wherein, by moving the in-transit securing means from the locking position into the release position, the lids of the reagent containers are each moved from the closed lid position into the other lid position, for example into an evaporation protection position. Typically, identical or similarly designed reagent containers are involved.

The reagent containers required for a test can thus be handled as a unit in an advantageous manner both in transit and upon insertion into the analysis system.

In this case, it can be provided for the reagent containers to be arranged in a row along the unlocking direction, wherein the lid axes of the lids mounted or provided on the reagent containers extend orthogonally to the unlocking direction.

In this way, it is possible to obtain reagent kits of elongate design in the unlocking direction, a plurality of which can be disposed in a spacing-saving manner for example on a turntable of the analysis system.

However, it should not be excluded that the reagent container assembly can comprise only one reagent container.

To simplify handling, particularly in the case of a plurality of reagent containers assembled to form a reagent container assembly, it can be provided that the reagent container assembly further comprises a reagent cartridge, on which the reagent container or containers is/are mountable or is/are provided.

Terms such as "top" and "bottom" refer in the following to a reagent container in its normal operating position.

FIG. 1 shows the individual parts of a reagent container 12 of a first typical embodiment of the present disclosure, namely a container body 13, as well as a closure 14 comprising a closure base member 16 and a lid 18 which is pivotally mountable on the closure base member 16 for pivotal movement about a lid axis 18a.

The individual parts 13, 16 and 18 may in each case be, for example, injection-molded parts, blow-molded parts or injection blow molded parts from a suitable plastics material.

The container body 13 comprises a central portion 20 of substantially parallelepipedal shape, a base portion 22 tapering towards the lower end of the container body 13 and an upper end portion 24 with a hollow cylindrical neck 26 and a parallelepipedal connecting part 28, on which four detent hooks 30 or detent projections are provided, which can engage in corresponding detent windows 32 of the closure base member 16, so that the closure base member 16 can be clipped onto the connecting part 28 of the container body 13.

In order to minimize the dead volume of the container body 13, i.e., the volume in which substance remains which cannot be removed from the reagent container 12 by a pipette of the analysis system, the base portion 22 tapers towards the lower end of the container body 13 so that the central axis M of the hollow cylindrical neck 26 passes through the lowest point of the container body 13.

The parallelepipedal shape of the central portion 20 is advantageous because it allows to arrange a plurality of reagent containers side-by-side or one behind the other in a space-saving manner, and because it allows, optionally, to apply information on the substances filled into the reagent containers to the walls of the central portion 20. This can be effected in that the reagent container 12, in particular the central portion 20, is sprayed or printed with color or a code (bar code), or in that suitable labels are applied. The information may, for example, comprise the filling substance and/or a batch identification or batch number. In this way, manual or automated assembly of a plurality of reagent containers to form a test kit is made possible.

Figure 4:
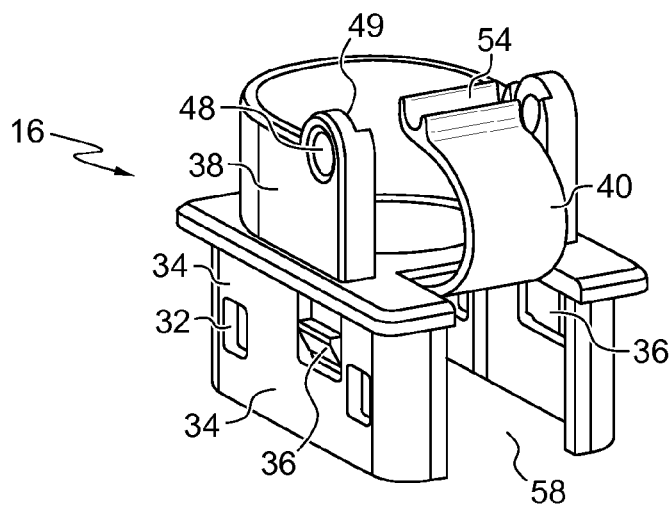
FIG. 4 shows another view of the closure base member in FIG. 3.
Figure 6:
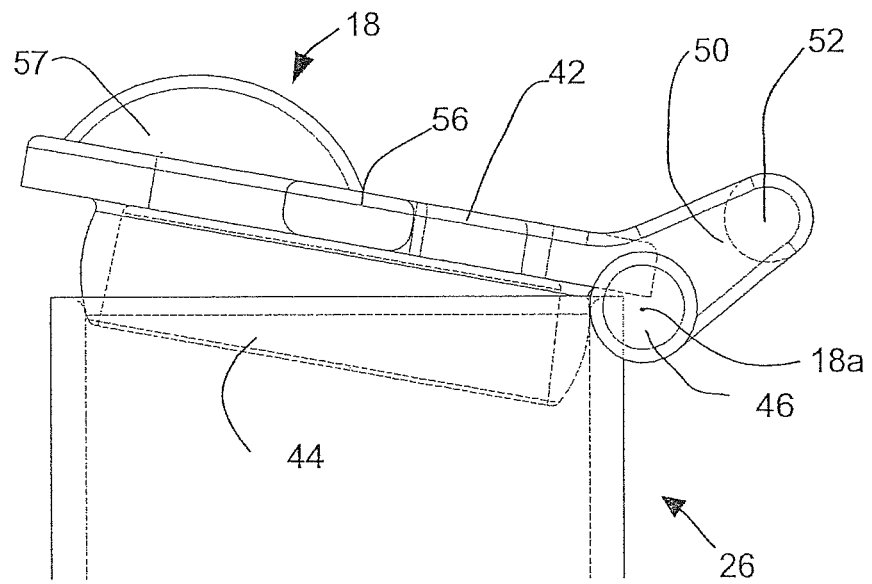
FIG. 6 shows the subject of FIG. 5 to illustrate the evaporation protection position.

The closure base member 16, which is illustrated in greater detail in FIGS. 3 and 4, comprises a lower connecting frame 34 in which the detent windows 32 and detent hooks 36 are provided for fastening the reagent container 12 in a reagent cartridge (cf., FIG. 9), as well as a lid mounting 38 on which the lid 18 can be inserted, so that it is rotatable about the lid axis 18a, and preloading means 40 which, in the present case, have the form of a U-shaped spring element and which, in the assembled condition of the reagent container 12, preload the lid 18 into the evaporation protection position shown in FIG. 6. In the present case, the closure base member 16 is formed in one piece with its above-described components, i.e., in particular with the connecting frame 34, the lid mounting 38 and the preloading means 40. However, it is also possible for these components to be produced separately and assembled to form the closure base member 16.

Furthermore, it is evident from the illustration in FIG. 4 that a recess 58, which, in the present case, is provided for production reasons, is provided in the lower connecting frame 34 below the preloading means 40. This recess is, however, optional.

As shown in FIG. 3, the lid 18 comprises a closure plate 42, an annular seal 44, two pivot journals 46 extending approximately parallel to the surface of the closure plate 42, which pivot journals 46 define the lid axis 18a and can be inserted into two bearing holes 48 of the lid mounting 38, as well as two lever arms 50 projecting at an obtuse angle from the closure plate 42 and joined together by a cross bar 52. The cross bar 52 can be fitted into a correspondingly formed jaw 54 provided on the preloading means 40. In order to facilitate the insertion of the pivot journals 46 of the lid 18 into the bearing holes 48 of the lid mounting 38, insert slopes 49 are provided in the lid mounting 38 above the bearing holes 48.

The lid 18 further comprises two mating elements 56 in the form of engagement tabs protruding away from the closure plate 42 approximately parallel to the lid axis 18a, as well as two securing elements 57 which are shaped in the form of circular segment plates and extend approximately perpendicular to the closure plate 42 and protrude upwards away from the latter. The function of the mating elements 56 and the securing elements 57 will be explained in more detail below with reference to FIGS. 14 and 16.

FIG. 2 shows the reagent container 12 from FIG. 1 in the assembled condition. Therein, the closure base member 16 is clipped on to the container body 13, the pivot journals 46 of the lid 18 are inserted into the corresponding bearing holes 48 of the lid mounting 38 and the cross bar 52 is fitted into the jaw 54 of the preloading means 40.

In the condition shown in FIG. 2, the lid 18 is situated in the in-transit securing position, in which the lid 18 is supported so firmly on the hollow cylindrical bottle neck 26 that, even if the reagent container 12 were to topple over, no substance could escape therefrom.

Figure 5:
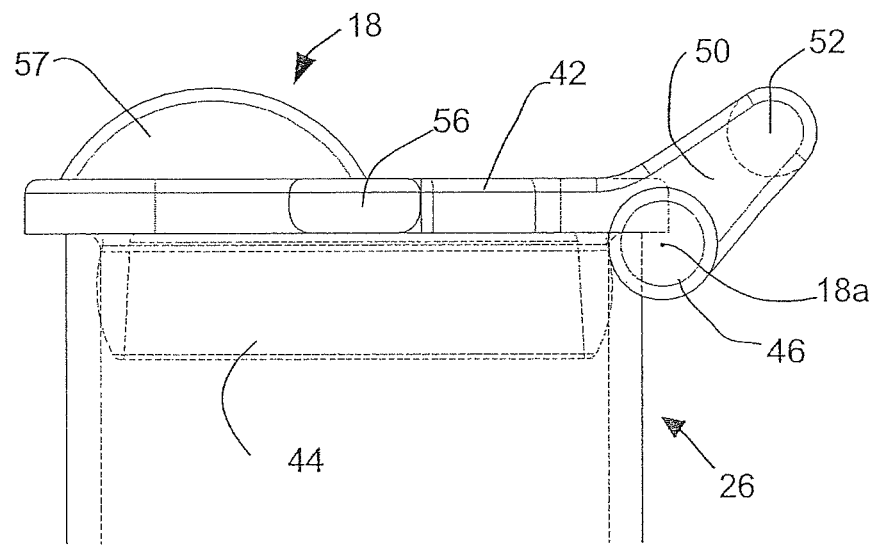
FIG. 5 shows a simplified illustration of parts of the closure and of the reagent container from FIG. 1 in a side view to illustrate the in-transit securing position.

FIG. 5 shows a side view of the lid 18 and of the hollow cylindrical bottle neck 26 in a schematic and slightly simplified illustration, in which the lid 18 is situated in the in-transit securing position. In this FIG. 5, hidden elements are shown in chain lines, so as to enable the interior of the structure to be viewed. For reasons of clarity, an illustration of the closure base member 16 has been omitted.

As is evident from this FIG. 5, the seal 44 is slightly convexly curved. Therefore, in the illustrated in-transit securing position, the lid 18 fluid tightly seals the hollow cylindrical bottle neck 26 and thus the reagent container 12.

FIG. 6 shows the subject of FIG. 5, wherein the lid 18 is situated in the evaporation protection position. In this case, the seal 44 rests only lightly on the rim of the hollow cylindrical bottle neck 26, which is sufficient to prevent evaporation of substance filling the reagent container 12 but at the same time allows the lid 18 to be opened with low force input.

Figure 7:
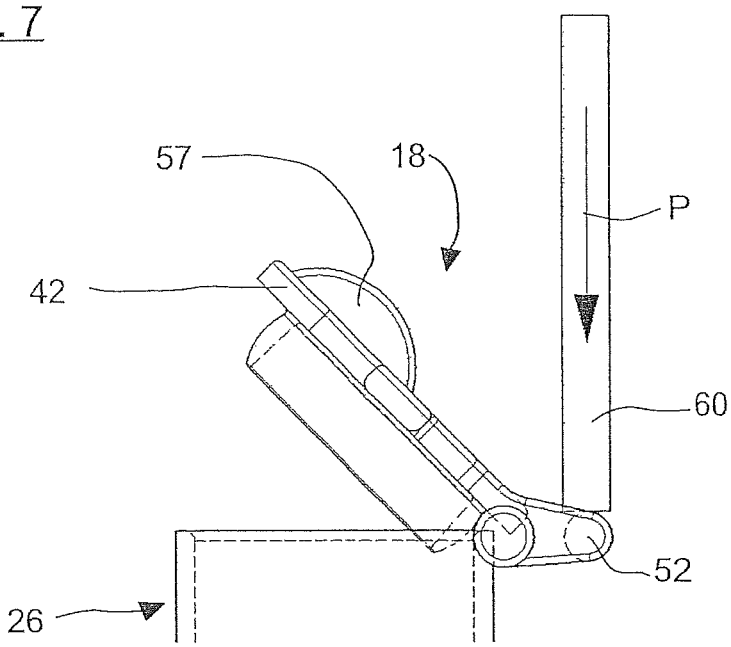
FIG. 7 shows the subject of FIG. 5 with the lid slightly opened by the analysis system.
Figure 8:
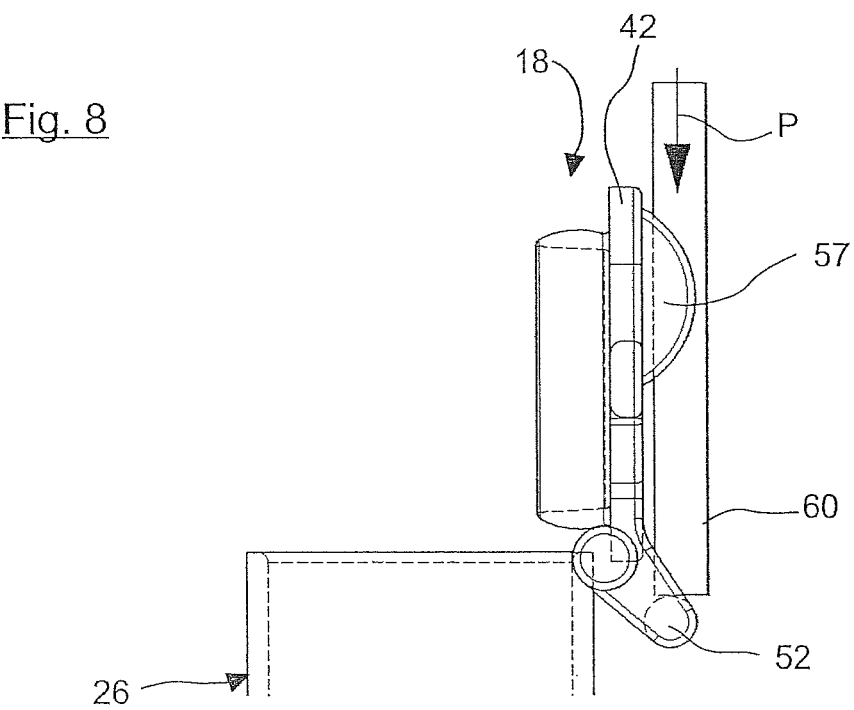
FIG. 8 shows the subject of FIG. 7 with the lid fully opened.

As illustrated in FIGS. 7 and 8, the reagent container 12 can be opened by a push rod 60 of an opening mechanism of an analysis system (not otherwise shown in more detail here), in that the push rod 60 presses the cross bar 52 of the lid 18 downwards in the direction indicated by an arrow P.

FIG. 7 shows the lid 18 in a slightly opened position; FIG. 8 shows the lid 18 in the fully opened positioned in which the closure plate 42 is pivoted through approximately 90° in relation to the in-transit securing position. The securing elements 57 are so arranged on the closure plate 42 that the push rod 60 of the analysis system extends precisely between the two locating elements 57, when the lid 18 is fully opened.

In the condition illustrated in FIG. 8, substance can now be removed from the reagent container 12 by the analysis system, usually by a pipette, and can be used for a test.

Figure 9:
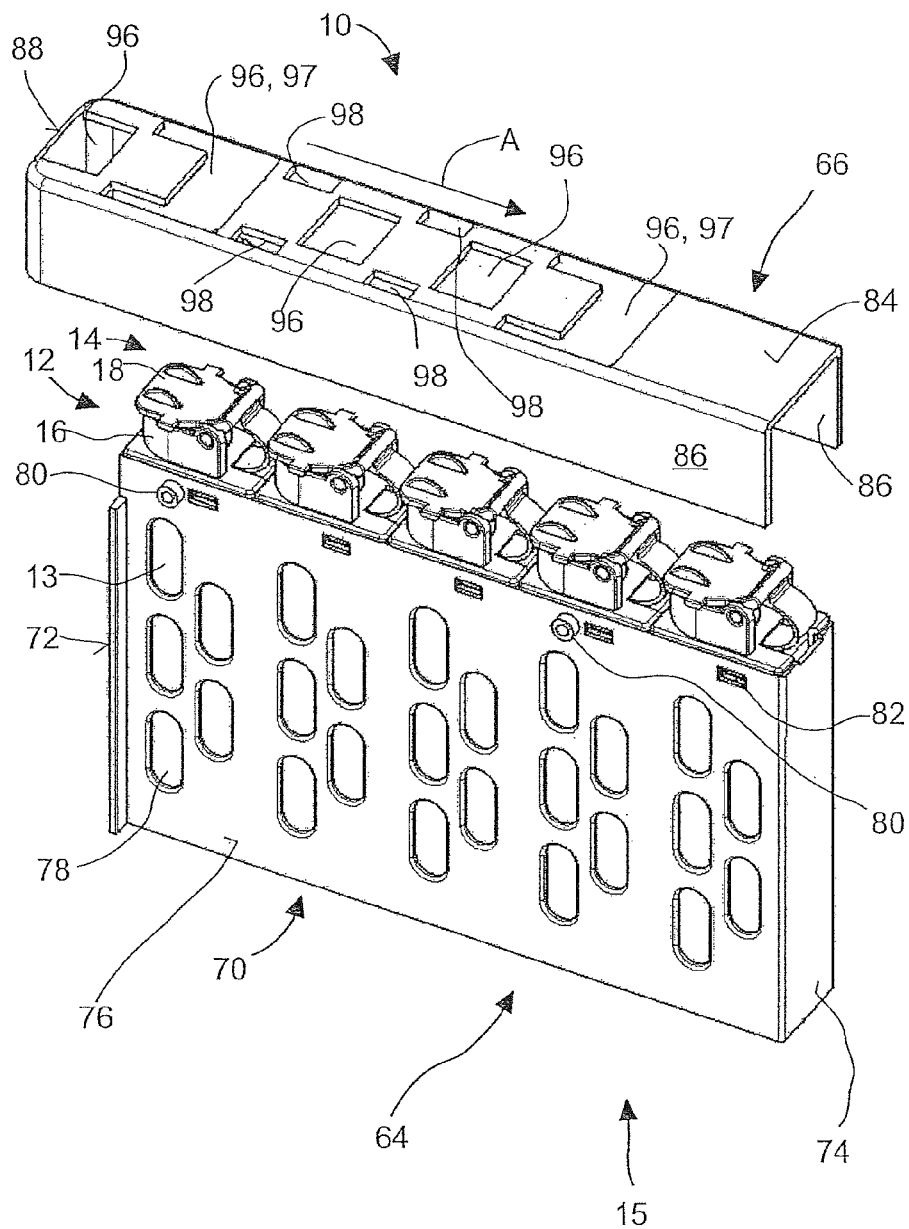
FIG. 9 shows a view in perspective of the first embodiment.
Figure 10:
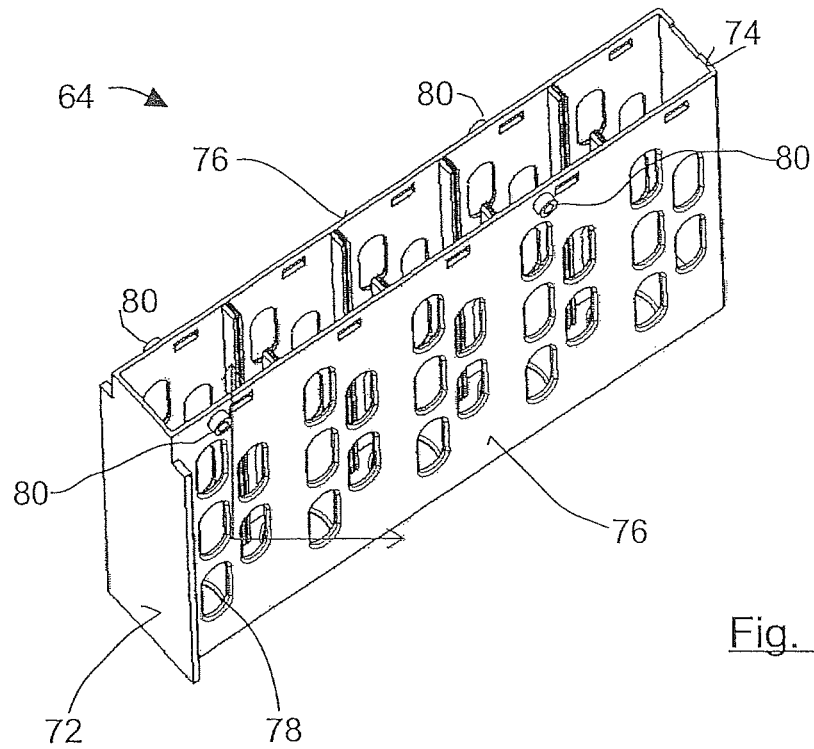
FIG. 10 shows the reagent cartridge from FIG. 9 in another view.

FIG. 9 shows a view in perspective of the reagent kit 10 according to an embodiment of the disclosure, which comprises a reagent container assembly 15 consisting, in the present case, of five substantially similar reagent containers 12 and a reagent cartridge 64, into which the reagent containers 12 are inserted and to which they are fastened, and which also comprises an in-transit securing means 66 which can be mounted in a locking position on the reagent container assembly 15 (cf., FIG. 12), in which locking position the in-transit securing means 66 secures the lids 18 in the respective in-transit securing position. In the illustration of FIG. 9, the in-transit securing means 66 is not (yet) mounted on the reagent container assembly 15.

The reagent cartridge 64 comprises a cartridge frame 70 with an end wall 72, a rear wall 74 and two side walls 76. The end wall 72 can be widened in relation to the rear wall 74, so that information in the form of an imprint and/or label and/or RFID chip or the like can be applied thereto. The widening of the end wall 72 can serve alternatively or additionally also as an orientation structure for correct positioning of the reagent cartridge in an analysis system.

In each of the side walls 76, there are provided openings 78 which serve to accelerate a thermal equilibrium between the substances filled into the reagent containers 12 and the environment. In the first embodiment illustrated here, these openings have the form of rounded rectangles. However, the number, shape and arrangement of the openings 78 can differ from the embodiment illustrated here. In particular, a reagent cartridge without such openings is also possible.

Moreover, on each side wall 76, there are provided two cylindrical engagement projections 80 which protrude outwards approximately orthogonally from the side walls 76 (i.e., away from the interior of the reagent cartridge 64).

As will be described in more detail below, these engagement projections 80 serve to fasten the in-transit securing means 66 to the reagent cartridge 64 and thus to the reagent container assembly 15.

Finally, in each side wall 76 and for each reagent container 12, a respective detent window 82 is provided, into which the corresponding detent hook 36 of the closure base member 16 can engage.

The in-transit securing means 66 has substantially the form of a hollow profile rail with U-shaped cross-section and with one closed end, i.e., it comprises an upper cover plate 84 with different recesses 96, 97, 98 provided therein, which will be described in more detail below, as well as two side plates 86 and an end plate 88. The end of the in-transit securing means 66 opposite the end plate 88 and also the underside thereof are open, so that the in-transit securing means 66 can be installed by sliding it onto the reagent cartridge 64 in the direction indicated by an arrow A.

Figure 11:
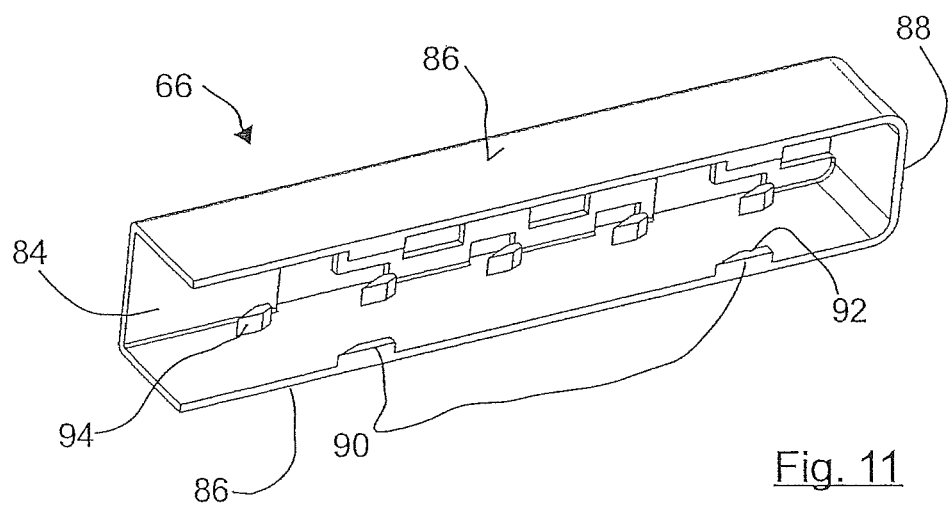
FIG. 11 shows the in-transit securing means from FIG. 9 in another view.

In this process, the engagement projections 80 come into sliding abutment engagement with engagement ramps 90 provided on the inside of the side plates 86 as illustrated in FIG. 11, so that upon sliding the in-transit securing means 66 in the direction A onto the reagent container assembly 15, the in-transit securing means 66 is pressed from above against the lids 18 of the reagent container assembly 15.

Figure 12:
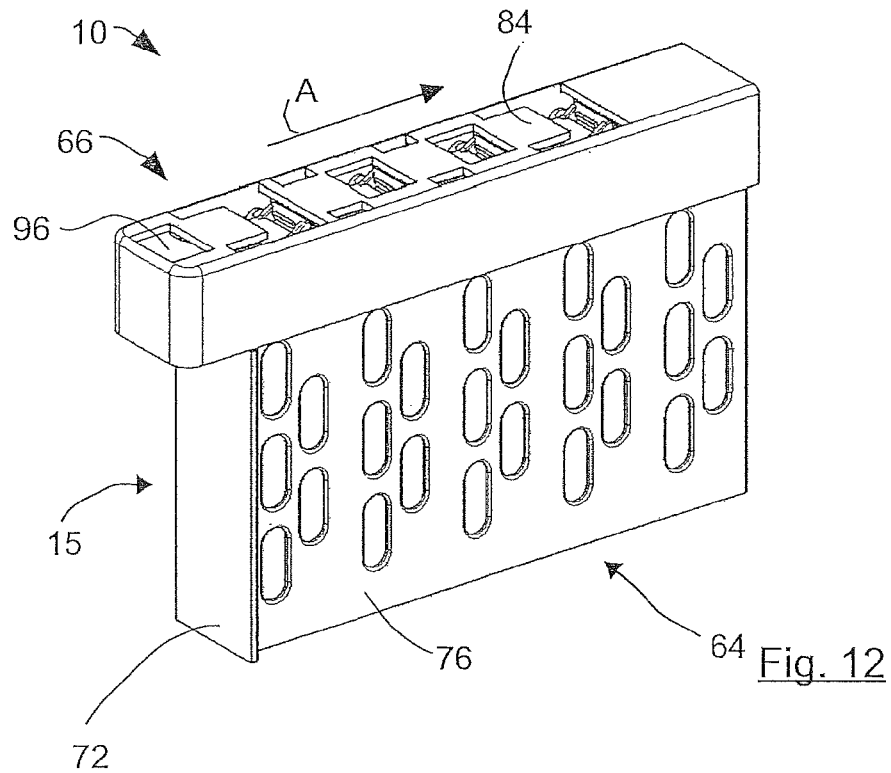
FIG. 12 shows the subject of FIG. 9 with the in-transit securing means mounted on the reagent container assembly in the locking position.
Figure 13:
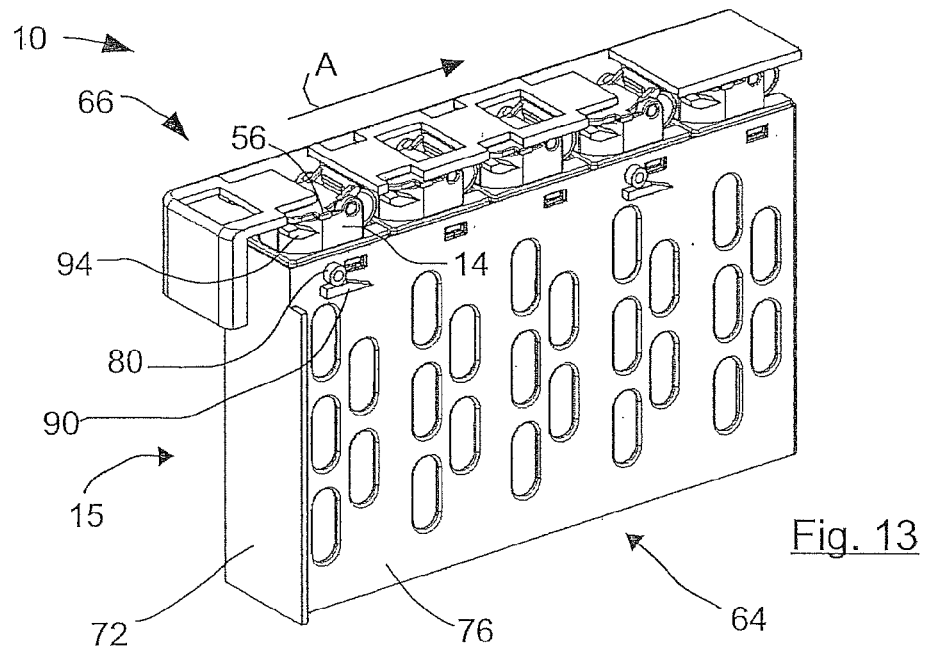
FIG. 13 shows the subject of FIG. 12, wherein a part of the in-transit securing means has been removed.

When the in-transit securing means 66 has reached the locking position illustrated in FIGS. 12 and 13, the engagement projections 80 engage in engagement depressions 92 provided on the engagement ramps 90.

As mentioned above, in FIGS. 12 and 13 the reagent kit according to an embodiment of the disclosure is illustrated in a condition, in which the in-transit securing means 66 is situated in the locking position.

FIG. 13 shows the subject of FIG. 12, wherein part of the in-transit securing means 66 has been removed so as to provide a better view of the closures 14 and the different engagement elements 90, 80, 94, 56.

As is evident from FIGS. 12 and 13, in this condition the closure plates 42 of the lids 18 are substantially covered by the cover plate 84 of the in-transit securing means 66. In this condition, the cover plate 84 presses from above against the securing elements 57, so that the lids 18 are each secured in the in-transit securing position and cannot be moved therefrom as long as the in-transit securing means 66 is situated in the locking position.

However, by further sliding the in-transit securing means 66 from the locking position in the direction A (the unlocking direction), the in-transit securing means 66 can be moved into its release position and the lids 18 can thus be displaced simultaneously into the respective evaporation protection position, as will be explained in more detail below with reference to FIGS. 14 to 16.

Figure 14:
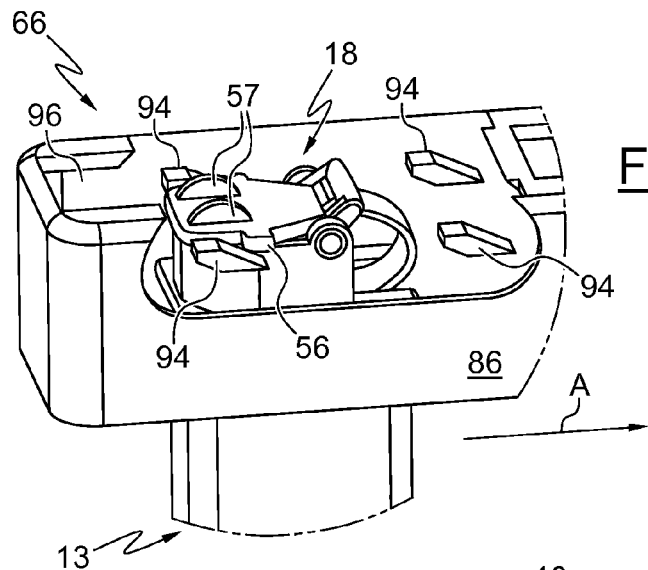
FIG. 14 shows a detail of the subject of FIG. 12 with the in-transit securing means partly removed.
Figure 15:
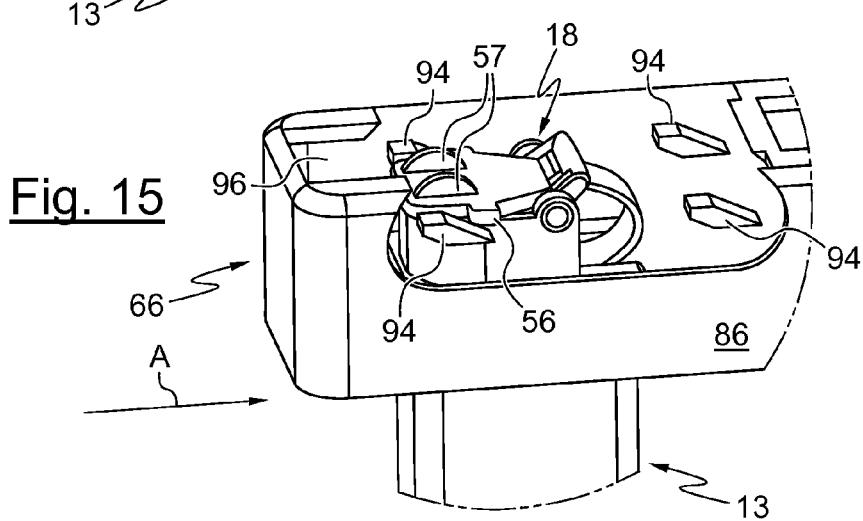
FIG. 15 shows the subject of FIG. 14, wherein the in-transit securing means is situated between the locking position and the release position.
Figure 16:
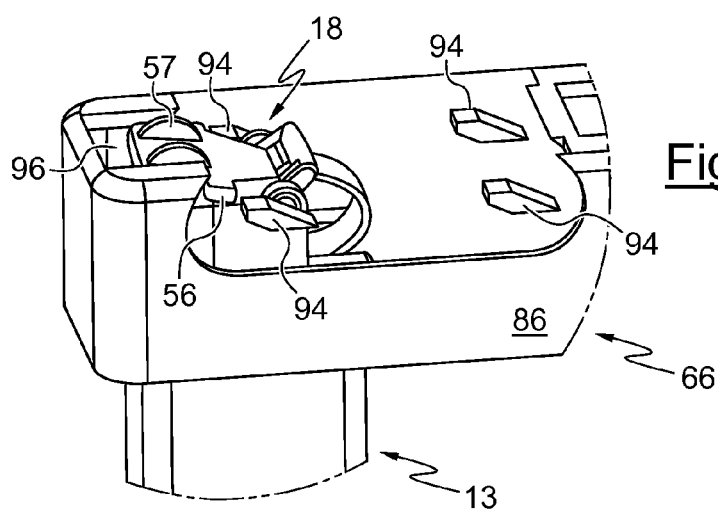
FIG. 16 shows the subject of FIG. 15, wherein the in-transit securing means is situated in the release position.

These FIGS. 14 to 16 each represent a part of that reagent container 12 of the reagent container assembly 15 which, in FIGS. 12 and 13, is nearest to the end wall 72 of the reagent cartridge 64, as well as a part of the in-transit securing means 66. A part of the cover plate 84 and a part of the side plate 86 nearer to the viewer have been removed from the in-transit securing means 66 so as to allow a view of the closure 14 of the reagent container 12 and also of the engagement elements 94. Moreover, for reasons of clarity, an illustration of the reagent cartridge has been omitted.

A respective ramp-shaped engagement element 94 is provided on the inside of each side plate 86 of the in-transit securing means 66 in the vicinity of the cover plate 84 for each reagent container 12, which engagement element 94, upon displacement of the in-transit securing means 66 relative to the reagent container assembly from the locking position in the unlocking direction A, comes into sliding abutment engagement with one of the mating elements 56 provided on the lid 18.

By further displacement of the in-transit securing means 66 in the unlocking direction A, as illustrated in FIG. 15, the lid 18 is raised by the ramp-shaped engagement elements 94 in cooperation with the associated mating elements 56 and is pivoted slightly in an opening direction.

In order to provide space for the securing elements 57 moving upwards in the process, an opening 96 is provided in the cover plate 84 of the in-transit securing means 66 for each of the lids 18.

Those openings 96, which, in the locking position, are arranged above the engagement projections 80, can be widened to form viewing windows 97 which enable the user to view the engagement projections 80 and thereby ascertain whether the in-transit securing means 66, is, for example, correctly fitted on the reagent cartridge 64 in the locking position.

Moreover, if desired, smaller viewing windows 98 (cf., FIG. 9) can also be provided above the ramp-shaped engagement elements 94 in the cover plate 84 of the in-transit securing means 66, which provide a view of the engagement elements 94 and enable a user to observe the cooperation between the engagement elements 94 and the mating elements 56. However, the widening of the openings 96 to form viewing windows 97 and the viewing windows 98 are not absolutely necessary.

Out of the release position illustrated in FIG. 16, the in-transit securing means 66 can be removed from the reagent cartridge 64. The reagent cartridge 64 with the reagent containers 12 disposed therein, i.e., the reagent container assembly 15, can subsequently be used in an automatic analysis system. The in-transit securing means 66 can be reused, for example by again being slid onto a reagent cartridge 64.

Since the lids 18 of the reagent containers 12 have already been moved from the in-transit securing position into the evaporation protection position by the removal of the in-transit securing means 66, it is now possible for the lids 18, as illustrated in FIGS. 7 and 8, to be opened with only slight force applied by the analysis system.

Even if, in the example illustrated in the Figures, the unlocking direction A corresponds to the direction in which the in-transit securing means is slid onto the reagent container assembly, it is of course also possible for the reagent kit to be configured so that the in-transit securing means is slid onto the reagent container assembly in a direction which extends in opposition to the unlocking direction, for example by the provision of engagement ramps on the in-transit securing means for fastening to the reagent container assembly, which ramps ascend in the other direction than the direction, in which the engagement ramps of the first embodiment ascend, and by the in-transit securing means being formed open at the end face.

In FIGS. 17 to 28, a reagent kit 110 according to a second exemplary embodiment of the present disclosure is illustrated. In these figures, features that correspond to those of the first exemplary embodiment illustrated in FIGS. 1 to 16 are denoted with reference numerals which result from adding the number 100 to the reference numerals of the corresponding features of the first exemplary embodiment. If letters are used as reference signs, the same letters are used in all embodiments.

In order to prevent unnecessary repetitions, the following figures will be described mainly in so far as they differ from the corresponding figures of the first exemplary embodiment. Otherwise, reference is made to the above description of the first embodiment shown in FIGS. 1 to 16.

Figure 17:
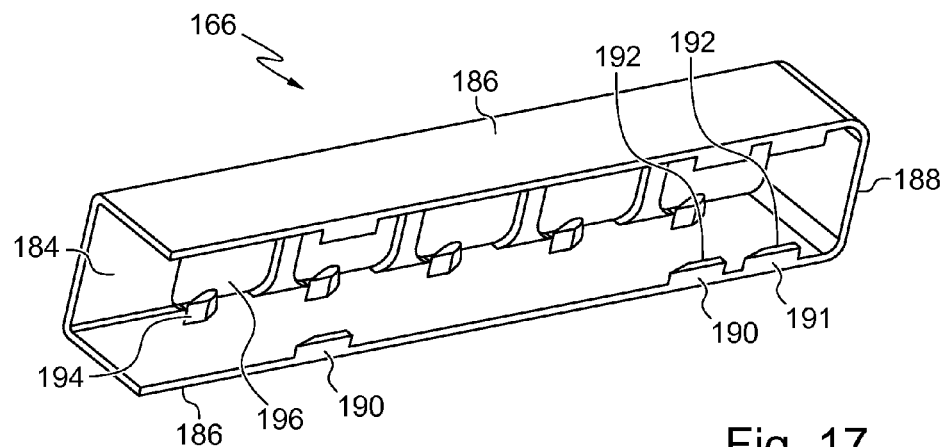
FIG. 17 shows the in-transit securing means of a second embodiment of the present disclosure in a perspective view corresponding to that of FIG. 11.

FIG. 17 shows the in-transit securing means 166 of the reagent kit 110 according to a second exemplary embodiment in a perspective view corresponding to that of FIG. 11. Therein, the portion of the cover plate 184 of the in-transit securing means 166, which presses the lids 118 down whilst in transit (i.e., in the locking position of the in-transit securing means 166), is reduced to narrow bars 185, while the openings 196 which correspond to the openings 96 of the example illustrated in FIGS. 1 to 16 are enlarged.

Furthermore, as can be seen from a comparison of FIGS. 17 and 11, the in-transit securing means 166 of the reagent kit 110 according to the second exemplary embodiment furthermore comprises an additional engagement ramp 191 provided on the inside of the side plate 186 of the in-transit securing means 166 near its end plate 188 and spaced apart only by a small distance from one of the engagement ramps 190 corresponding to those of the first exemplary embodiment.

Figure 18:
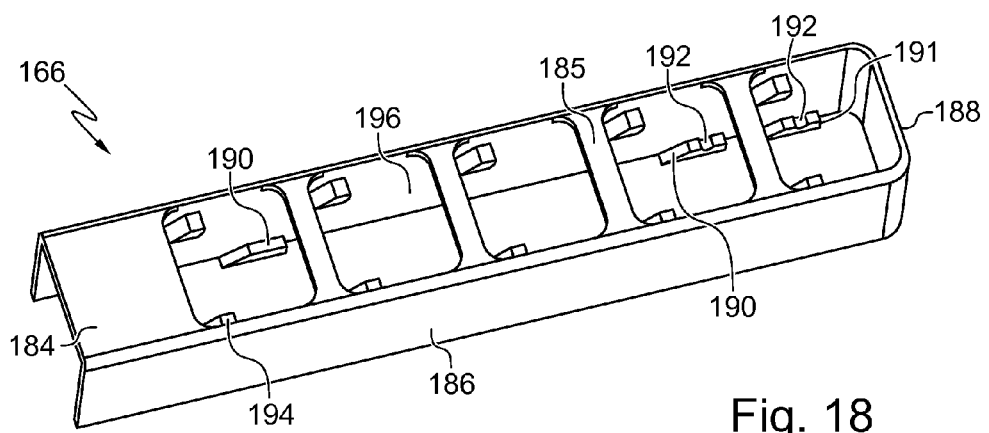
FIG. 18 shows the subject of FIG. 17 in another perspective view.

FIG. 18 shows the in-transit securing means 166 in a different perspective view revealing that also the additional engagement ramp 191 is provided with an engagement depression 192.

Figure 19:
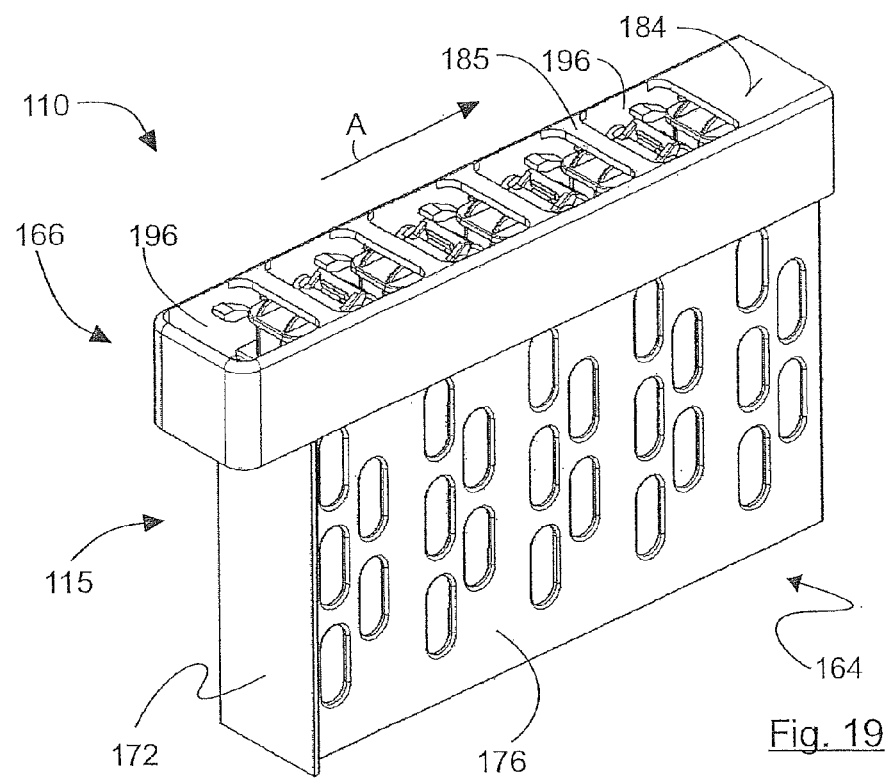
FIG. 19 shows the reagent kit according to the second embodiment of the present disclosure with the in-transit securing means mounted on the reagent container assembly in the locking position.
Figure 20:
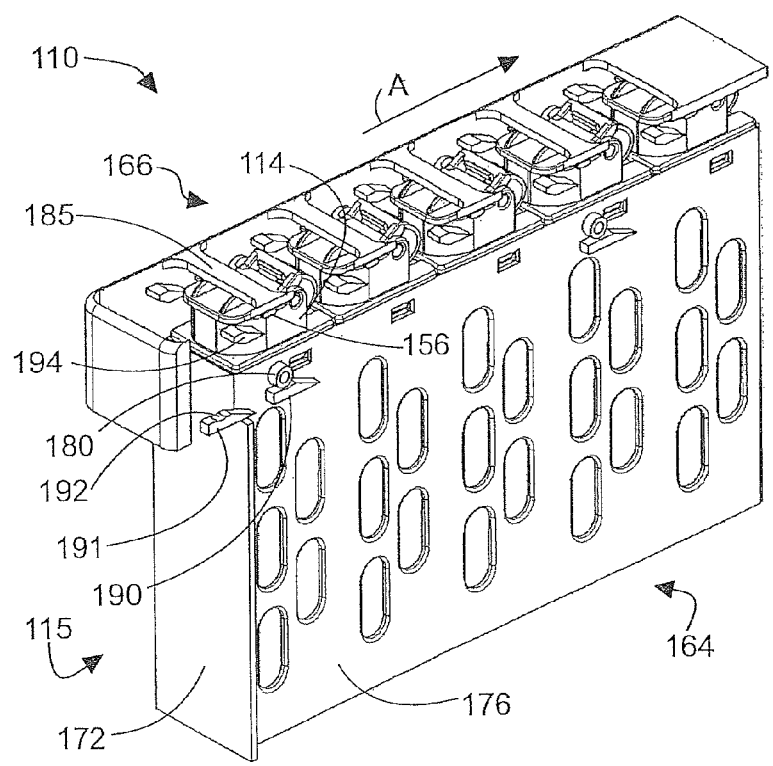
FIG. 20 shows the subject of FIG. 19, wherein a part of the in-transit securing means has been removed.

FIGS. 19 and 20 correspond to FIGS. 12 and 13 and show the reagent kit 110 with the in-transit securing means 166 mounted on the reagent container assembly 115 in the locking position, wherein in FIG. 13 the side plate 186 of the in-transit securing means 166 nearer to the viewer is removed in order to allow an uninhibited view of the interplay between the in-transit securing means 166 and the reagent container assembly 115.

In the locking position, the narrow bars 185 of the cover plate 184 are positioned directly above the securing elements 157 of the lids 118 of the reagent containers 112, securing the lids 118 in the in-transit securing position. The two engagement projections 180 provided on the side-walls 176 of the cartridge frame 170 near to the end wall 172 thereof rest in respective engagement depressions 192 provided in the corresponding engagement ramps 190, ensuring that the in-transit securing means 166 is not involuntarily shifted from the locking position to the release position. With the in-transit securing means 166 mounted on the reagent container assembly 115 in the locking position, the reagent kit can be safely transported, e.g., from the manufacturer to the user.

Although in this embodiment only the engagement ramps 190 near to the end plate 188 have engagement projections 192, it is also possible to provide similar engagement depressions on all engagement ramps 190.

Figure 21:
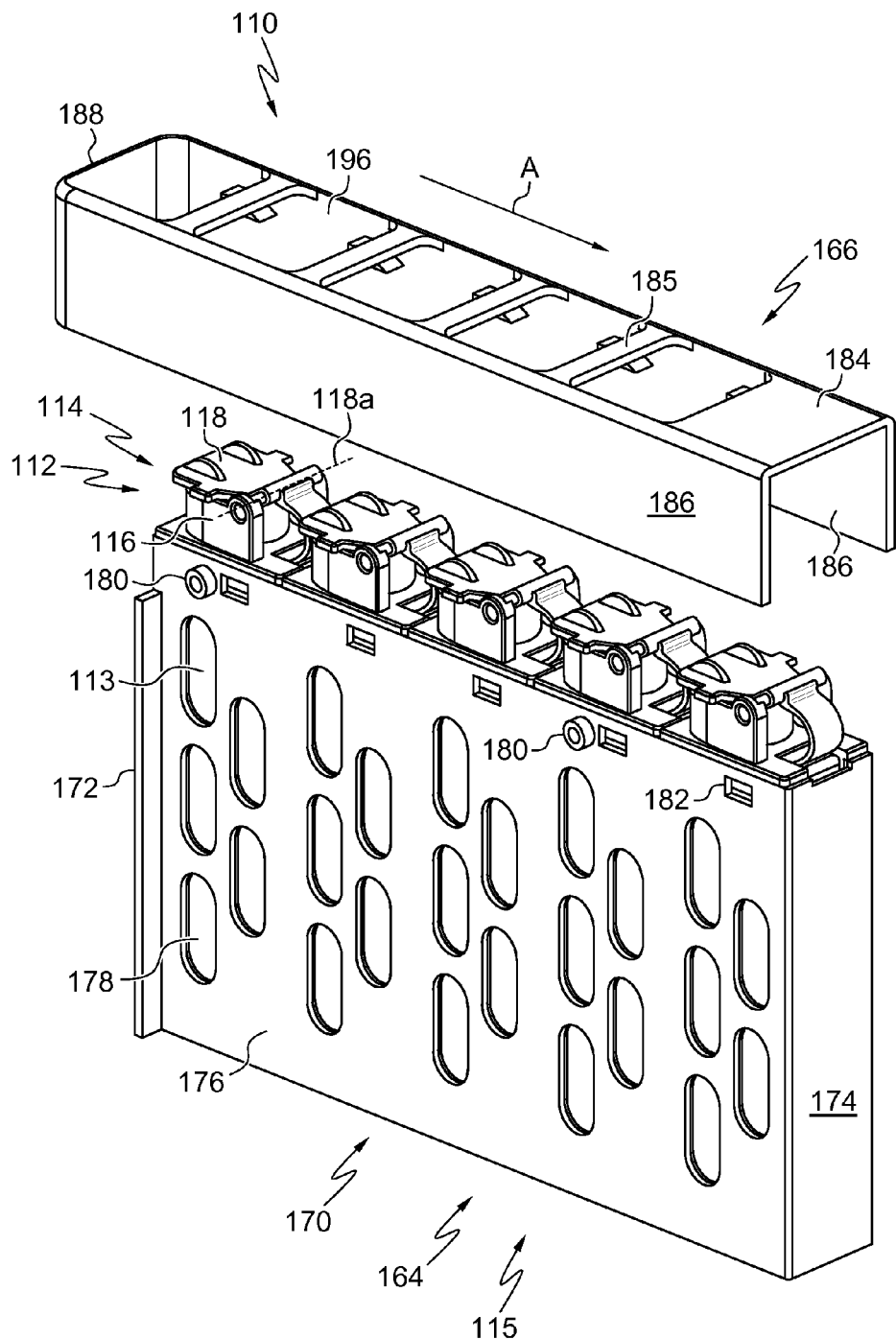
FIG. 21 shows a view in perspective of the reagent kit according to the second embodiment of the present disclosure.

FIG. 21 shows a view in perspective of the reagent kit 110 according to the second embodiment of the present disclosure, wherein the in-transit securing means 166 is not yet mounted on the reagent container assembly 115. With respect to the details, reference is made to the description of the corresponding FIG. 9 of the first exemplary embodiment.

Figure 22:
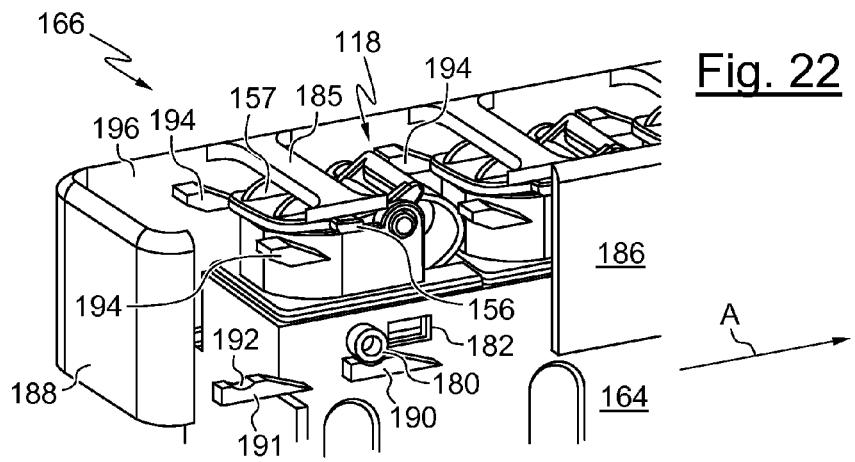
FIG. 22 shows a detail of the subject of FIG. 19 with the in-transit securing means partly removed.
Figure 23:
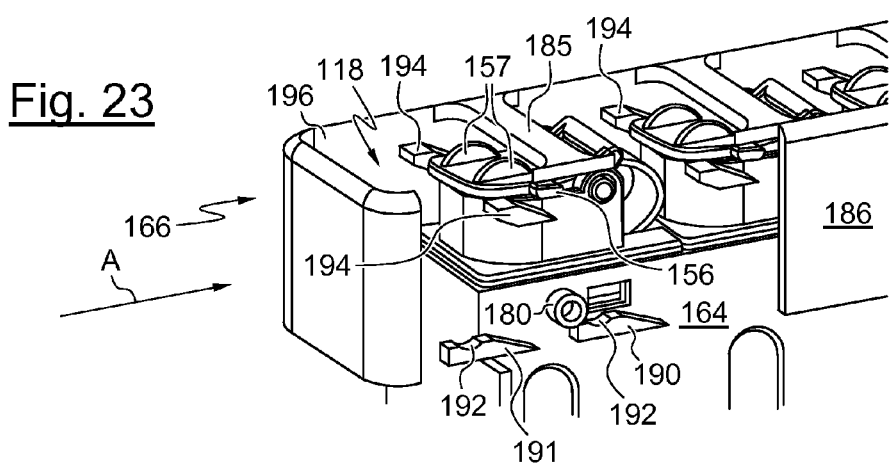
FIG. 23 shows the subject of FIG. 22, wherein the in-transit securing means is situated between the locking position and the release position.
Figure 24:
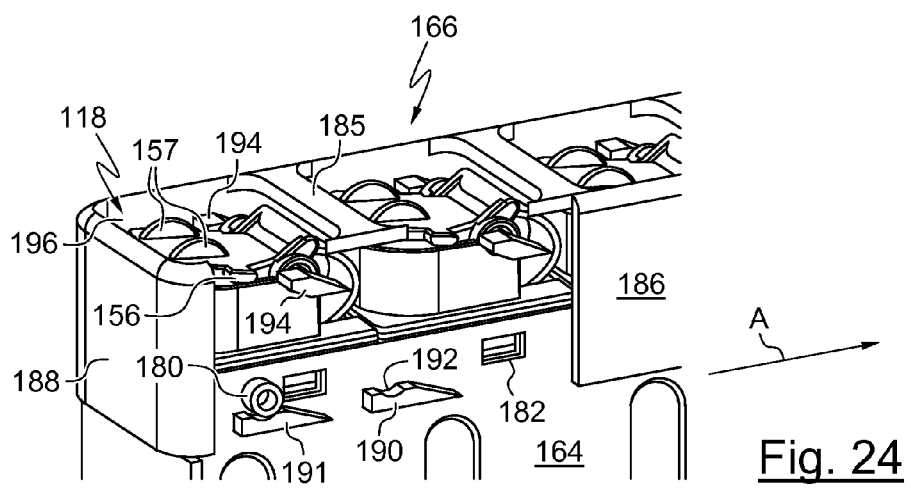
FIG. 24 shows the subject of FIG. 23, wherein the in-transit securing means is situated in the release position.

FIGS. 22 to 24 correspond to FIGS. 14 to 16, with the exception that in FIGS. 22 to 24 also parts of the reagent cartridge 164 are shown. The Figures illustrate how the in-transit securing means 166 is moved from the locking position (FIG. 22) by sliding it with respect to the reagent container assembly 115 in the unlocking direction A (FIG. 23) so that the mating elements 156 provided on the lids 118 come into engagement with the ramp-shaped engagement elements 194 provided on the inside of the in-transit securing means 166, sliding upwards these ramp-shaped engagement elements 194 and being thus lifted upwards, moving the lids 118 from the closed lid position towards the evaporation protection position, until the in-transit securing means 166 has reached the release position (FIG. 24), in which the narrow bars 185 of the upper cover plate 184 are positioned between adjacent lids 118 and all lids 118 are in the evaporation protection position. In the release position, the two engagement projections 180 provided on the side walls 176 of the cartridge frame 170 near its end wall 172 rest in corresponding engagement depressions 192 provided on the additional engagement ramps 191.

Figure 25:
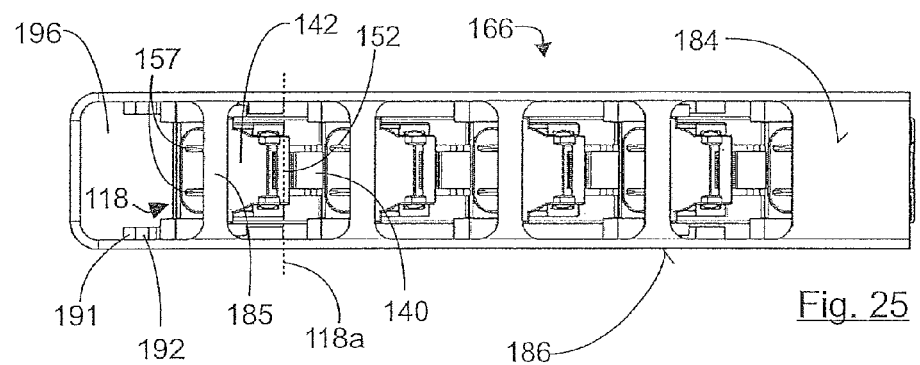
FIG. 25 shows the subject of FIG. 22 in a top view.
Figure 26:
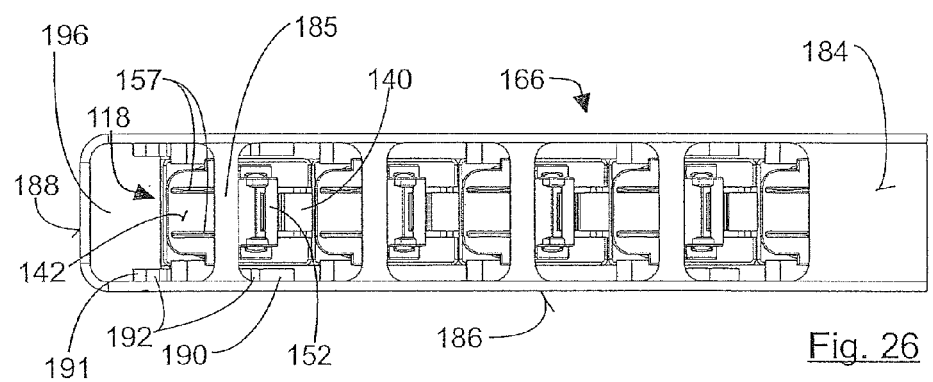
FIG. 26 shows the subject of FIG. 23 in a top view.
Figure 27:
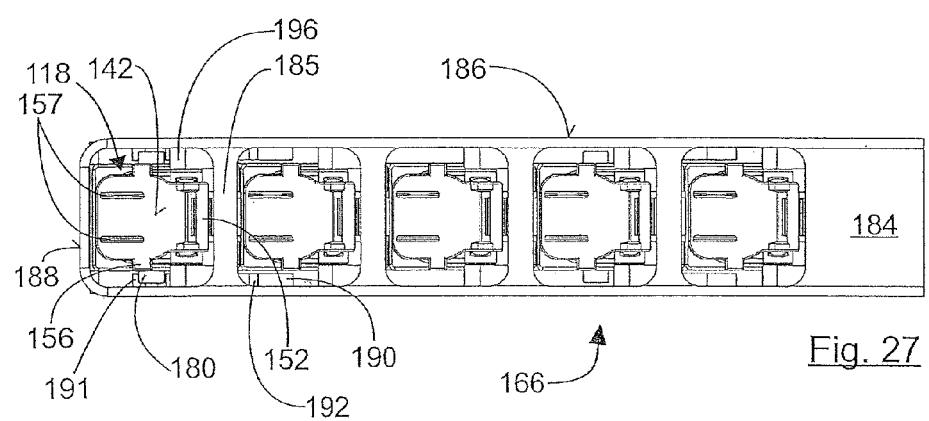
FIG. 27 shows the subject of FIG. 24 in a top view.

FIGS. 25 to 27 show top views of the subject of FIGS. 22 to 24.

Figure 28:
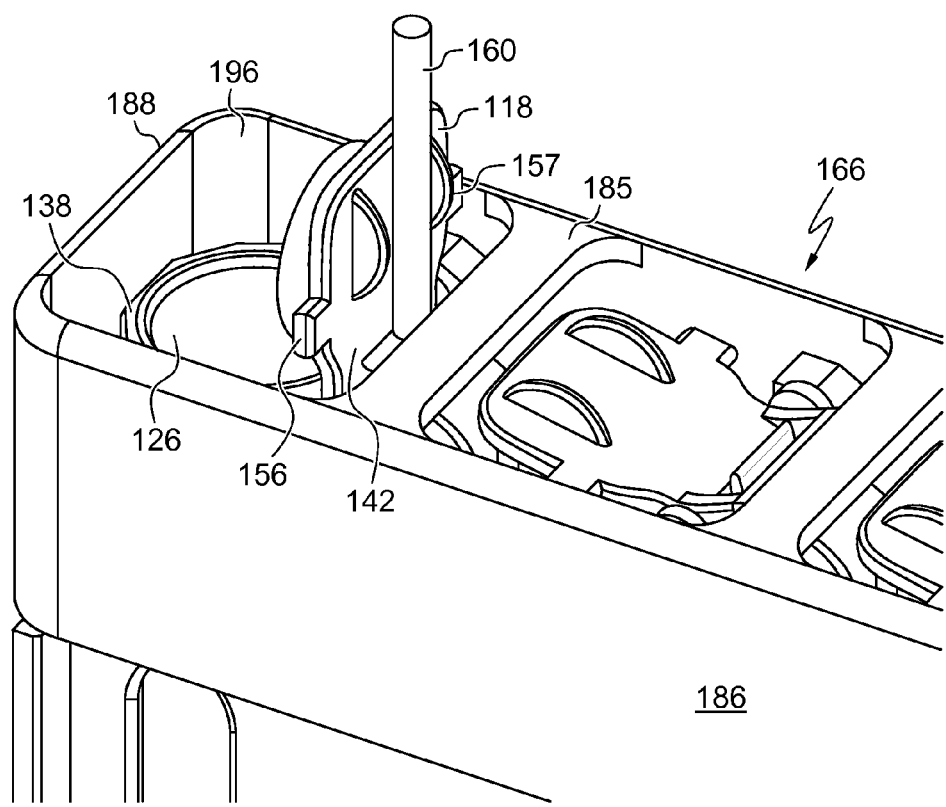
FIG. 28 shows a part of the reagent kit according to the second embodiment of the disclosure wherein the lid of one of the reagent containers is opened by the push rod of an analysis system.

In summary, in the reagent kit 110 of the second exemplary embodiment, the openings 196 provided on the upper cover plate 184 of the in-transit securing means 166 are enlarged to such an extent that, in the release position of the in-transit securing means 166, opening of the lids 118 by the analysis system is possible even with the in-transit securing 166 means remaining on the reagent container assembly 115 as it is illustrated in FIG. 28, showing one of the lids 118 being opened by the push rod 160 of an analysis system (otherwise not shown here). The bars 185 of the upper cover plate 184 are positioned in the release position exactly between adjacent lids 118 so that they do not impede the opening of the lids 118. An in-transit securing means of this type can remain permanently on the reagent container assembly 115, in particular also during analysis operation.

In order to limit the displacement travel between the locking position and the release position, according to a further variation of the first or second exemplary embodiment (not shown here), it may be provided for the bars to be moved during the unlocking over the free lid end opposite the respective lid axis, i.e., in exactly the opposite direction, as in the embodiments illustrated in the Figures. For this purpose, the ramp-shaped engagement elements of the in-transit securing means, which lift the lids in cooperation with the mating elements 56 during the unlocking, can be formed at a slightly different location and with ramps ascending in the respectively different direction than the direction in which the ramps of the engagement elements 94, 194 of the first and the second exemplary embodiment ascend. In this way, the displacement travel can be limited to approximately 5 to 7 mm.

Finally, in all the embodiments described, it is possible to provide further detent elements on the in-transit securing means and the reagent container assembly so as to prevent unintentional movement of the in-transit securing means from the locking position and/or from the release position.

It is noted that terms like "preferably", "commonly", and "typically" are not utilized herein to limit the scope of the claimed subject matter or to imply that certain features are critical, essential, or even important to the structure or function of the embodiments disclosed herein. Rather, these terms are merely intended to highlight alternative or additional features that may or may not be utilized in a particular embodiment of the present disclosure.

It is also noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

It will be apparent to those skilled in the art that various equivalents, changes, and modifications may be made to the embodiments described herein without departing from the spirit and scope of the claimed subject matter. Thus it is intended that the specification cover the modifications and variations of the embodiments described herein provided such modifications and variations come within the scope of the appended claims and their equivalents.

What is claimed is:

1. A reagent kit comprising:
   a reagent container assembly with at least one reagent container for accommodating a substance, the reagent container including at least one container body and at least one closure which is associated with the container body and which is mountable or provided thereon, wherein the closure comprises a closure base member and a lid supported pivotally on the closure base member for pivotal movement around a lid at least between a closed lid position and another lid position; and
   an in-transit securing means formed separately from the reagent assemble and from the lid, the in-transit securing means being reversibly coupled to the reagent container assembly in a locking position in which the in-transit securing means secures the lid in the closed lid position and wherein, when coupled to the reagent container assembly, the in-transit securing means is movable by sliding displacement relative to the reagent container assembly in a linear movement in an unlocking direction (A) from the locking position into a release position, wherein the in-transit securing means comprises at least one ramp-shaped engagement element and the lid comprises at least one mating element adapted to cooperate with the engagement element in such a way that, upon sliding displacement of the in-transit securing means mounted on the reagent container assembly from the locking position in the unlocking direction (A), the engagement element and the mating element are in mutual sliding abutment engagement or come into mutual sliding abutment engagement, so that, by sliding displacement of the in-transit securing means in the linear movement in the unlocking direction (A) from the locking position into the release position, the lid is pivoted from the closed lid position into the other lid position.

2. The reagent kit according to claim 1, wherein the in-transit securing means is removable from the reagent container assembly out of the release position.

3. The reagent kit according to claim 1, wherein the other lid position is an opened lid position.

4. The reagent kit according to claim 1, wherein the other lid position is an evaporation protection position and the closed lid position is an in-transit securing position, wherein the lid is movably supported on the closure base member for movement between the in-transit securing position, the evaporation protection position and an opened lid position.

5. The reagent kit according to claim 3 further comprising a preloading means for preloading the lid from the opened lid position towards the closed lid position.

6. The reagent kit according to claim 4 further comprising a preloading means for preloading the lid from the opened lid position towards the evaporation protection position.

7. The reagent kit according to claim 5, wherein the preloading means are formed in one piece with the closure base member.

8. The reagent kit according to claim 6, wherein the preloading means are formed in one piece with the closure base member.

9. The reagent kit according to claim 1, wherein the reagent container assembly comprises a plurality of reagent containers, and wherein, by moving the in-transit securing means from the locking position into the release position, the lids of the reagent containers are each moved from the closed lid position into the other lid position.

10. The reagent kit according to claim 9, wherein the plurality of reagent containers comprises 3 to 5 reagent containers.

11. The reagent kit according to claim 9, wherein the reagent containers are arranged in a row along an unlocking direction (A), and wherein a lid axis of the lids mounted or provided on the reagent containers extend substantially orthogonally to the unlocking direction (A).

12. The reagent kit according to claim 1, wherein the reagent container assembly further comprises a reagent cartridge, on which the reagent container or the reagent containers is/are mountable or provided.

13. The reagent kit according to claim 1, wherein the at least one container body is reversibly coupled to the at least one closure.

14. The reagent kit according to claim 1, wherein the in-transit securing means has the form of a hollow profile rail with a U-shaped cross-section, including two side plates, the at least one ramp-shaped engagement element being provided on the inside of one of the side plates.

* * * * *